(12) United States Patent
Skaling et al.

(10) Patent No.: US 8,513,958 B2
(45) Date of Patent: Aug. 20, 2013

(54) STACKED SENSOR FOR TESTING A POROUS MEDIUM

(75) Inventors: Whitney Skaling, Buellton, CA (US); Steve Riley, Summerland, CA (US)

(73) Assignee: Soilmoisture Equipment Corporation, Goleta, CA (US)

( * ) Notice: Subject to any disclaimer, the term of this patent is extended or adjusted under 35 U.S.C. 154(b) by 251 days.

(21) Appl. No.: 13/160,029

(22) Filed: Jun. 14, 2011

(65) Prior Publication Data
US 2012/0319704 A1 Dec. 20, 2012

(51) Int. Cl.
*G01R 27/26* (2006.01)
*G01R 31/28* (2006.01)

(52) U.S. Cl.
USPC .................... 324/658; 324/600; 324/529

(58) Field of Classification Search
None
See application file for complete search history.

(56) References Cited

U.S. PATENT DOCUMENTS 5,703,299 A * 12/1997 Carleton et al. ............ 73/863.83
6,946,833 B1 * 9/2005 Logue et al. .................. 324/240

* cited by examiner

*Primary Examiner* — Jermele M Hollington
*Assistant Examiner* — Trung Nguyen
(74) *Attorney, Agent, or Firm* — Lyon & Harr, LLP; Richard T. Lyon (57) ABSTRACT

A sensor is provided for testing a porous medium. The sensor includes a plurality of porous elements, a number of electrically conductive interface plates which is one greater than the quantity of elements, and the same number of conductors. Each element operates as a discrete variable capacitor, exhibits a different known liquid release curve, and includes a first axial opening. The elements are stacked one on top of another. Each plate includes a second axial opening. The plates are axially distributed within the sensor such that the first and second axial openings combine to form a longitudinal cavity that extends from the sensor's proximal end to its distal end, and each element is sandwiched between a different pair of plates. A distal end of each conductor is attached to a different one of the plates, and a proximal end is routed through the cavity to the sensor's proximal end.

26 Claims, 7 Drawing Sheets

STACKED SENSOR FOR TESTING A POROUS MEDIUM

BACKGROUND

A probe or sensor is commonly used to test a medium of interest. The probe/sensor is disposed in the medium being tested. The testing generally determines various properties of the medium and optionally monitors the medium on an ongoing basis to automatically detect changes in its properties. The design and configuration of the probe/sensor are commonly adapted to the specific type of medium being tested and the specific type(s) of medium properties being determined.

SUMMARY

This Summary is provided to introduce a selection of concepts, in a simplified form, that are further described hereafter in the Detailed Description. This Summary is not intended to identify key features or essential features of the claimed subject matter, nor is it intended to be used as an aid in determining the scope of the claimed subject matter.

Stacked sensor embodiments described herein generally involve a sensor for testing a porous medium. In one exemplary embodiment the sensor includes a plurality of porous ceramic elements. Each element operates as a discrete variable capacitor. Each element also exhibits a different known liquid release curve. Each element also includes a first axial opening. The elements are stacked one on top of another such that the radial axis of each element is positioned along a common axis. The sensor further includes a first number of electrically conductive interface plates, where the first number is one greater than the total quantity of elements. Each plate includes a second axial opening. The plates are axially distributed within the sensor such that the radial axis of each plate is positioned along the common axis, the first axial openings of the elements combine with the second axial openings of the plates to form a longitudinal cavity within the sensor which is centered along the common axis and extends from a proximal end of the sensor to a distal end of the sensor, and each element is sandwiched between a different pair of plates such that substantial electrical contact is established between the element and both plates in the pair. The sensor yet further includes a second number of electrical conductors, where the second number equals the first number. A distal end of each conductor is electrically attached to a different one of the plates. A proximal end of each conductor is routed through the longitudinal cavity to the proximal end of the sensor. In another exemplary embodiment porous hydrophobic elements can be used in place of the porous ceramic elements.

In yet another exemplary embodiment the sensor includes a plurality of the ceramic elements, a third number of non-porous and electrically non-conductive insulating elements, a fourth number of the electrically conductive interface plates, and a fifth number of the electrical conductors. The third number is one less than the total quantity of ceramic elements, the fourth number is twice this total quantity, and the fifth number equals the fourth number. Each insulating element includes a third axial opening. The radial axis of each of the insulating elements and each of the ceramic elements is positioned along a common axis. The insulating elements are interleaved between the ceramic elements such that each insulating element is sandwiched between a different pair of ceramic elements. The interface plates include one half the fourth number of upper plates and one half the fourth number of lower plates. The interface plates are axially distributed within the sensor such that the radial axis of each interface plate is positioned along the common axis, the first axial openings of the ceramic elements combine with the third axial openings of the insulating elements and the second axial openings of the interface plates to form the aforementioned longitudinal cavity within the sensor, and each ceramic element is sandwiched between a different upper plate and lower plate such that substantial electrical contact is established between the ceramic element and both the upper and lower plates.

DESCRIPTION OF THE DRAWINGS

The specific features, aspects, and advantages of the stacked sensor embodiments described herein will become better understood with regard to the following description, appended claims, and accompanying drawings where:

DETAILED DESCRIPTION

In the following description of stacked sensor embodiments reference is made to the accompanying drawings which form a part hereof, and in which are shown, by way of illustration, specific embodiments in which the stacked sensor can be practiced. It is understood that other embodiments can be utilized and structural changes can be made without departing from the scope of the stacked sensor embodiments.

1.0 Stacked Sensor for Testing a Porous Medium

Generally speaking, the stacked sensor embodiments described herein are applicable to testing a porous medium. More particularly, the stacked sensor embodiments can measure one or more dielectric influences in the medium and/or one or more characteristics of the medium. Exemplary dielectric influences in the medium which can be measured include the volumetric liquid content of the medium and the salinity of the medium (i.e., the concentration of salt in the medium), among other things. Exemplary characteristics of the medium which can be measured include the temperature of the medium, the fluid holding capabilities of the medium (e.g., the open pore space of the medium), and other detectable physical or chemical properties of the medium.

The stacked sensor embodiments described herein are advantageous for a variety of reasons including, but not limited to, the following. Very precise measurements of the dielectric influences in the porous medium can be made even when the medium has a very small content of the dielectric influences. The measurements can be made and then analyzed very quickly. The measurements can be made and analyzed either once at a particular point in time, or on an ongoing basis over a period of time using automation. Thus, the medium can be continually monitored and any changes in its properties can be automatically detected.

Furthermore, a wide variety of different types of porous media can be tested such as soil (which may include substances such as clay, sediments and organic matter), wood, rock, concrete, slurries of various sorts, foodstuffs, or grains, among other things. The media can be tested in situ (e.g., one or more stacked sensors can be disposed at different locations in a farm field or the like), or a sample of the media can be taken (such as a core sample or the like) and subsequently tested in a different setting such as a laboratory environment or the like. Additionally, a wide variety of different types of liquids having different dielectric natures can be measured such as water, oil, milk, glycol, or honey, among other things. The liquid being measured can also be any homogenized mixture of different substances in liquid form.

1.1 System Environment

Figure 1:
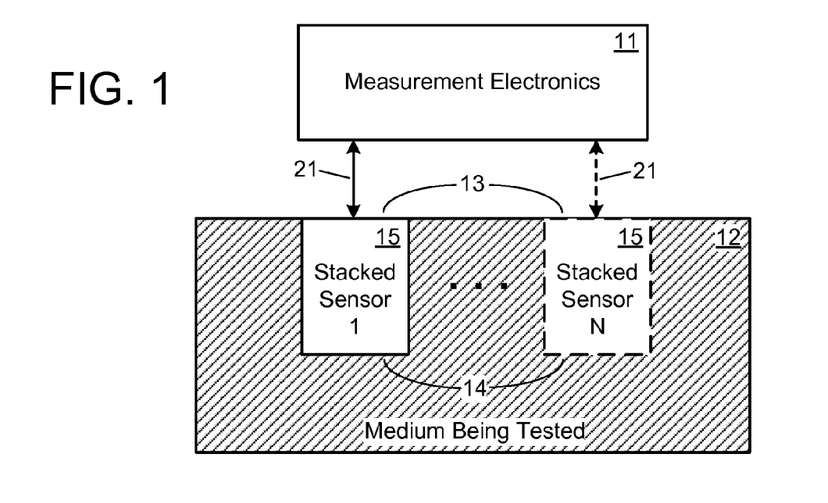
FIG. 1 is a diagram illustrating an exemplary embodiment, in simplified form, of a system for implementing the stacked sensor embodiments described herein.

FIG. 1 illustrates an exemplary embodiment, in simplified form, of a suitable system environment in which the stacked sensor embodiments described herein can be implemented. The environment illustrated in FIG. 1 is just one example of a suitable system environment and is not intended to suggest any limitation as to the scope of use or functionality of the stacked sensor embodiments. Neither should the system environment be interpreted as having any dependency or requirement relating to any one or combination of the components discussed hereafter in this section.

As exemplified in FIG. 1, a suitable system environment for implementing the stacked sensor embodiments described herein generally includes the following components. One or more stacked sensors 15 are disposed within a porous medium which is being tested 12. In the situation where a plurality of sensors 15 are used, each of the sensors can be disposed at a different location within the medium 12 so as to provide an analysis of the medium which covers a larger vertical and/or horizontal area. In an alternate embodiment of the stacked sensor (not shown), rather than a plurality of sensors being individually disposed at different locations within the medium as just described, a plurality of sensors can also be disposed at different axial positions within an insertion device (such as a tube, among other things) which is disposed within the medium. It will be appreciated that this particular embodiment can be used in various ways such as testing the medium at a prescribed number of different depths.

Referring again to FIG. 1, measurement electronics 11 are electrically connected 21 to the proximal end 13 of each of the stacked sensors 15. As will be described in more detail hereafter, each of the electrical connections 21 includes a number of electrical conductors each of which is electrically attached to a different electrically conductive interface plate included within the sensor 15. Each of the electrical connections 21 can optionally also include an additional pair of electrical conductors which are electrically attached to a temperature sensing device which can optionally be included within the sensor 15. The measurement electronics 11 interoperate with each of the sensors 15 individually in a time-shared manner to test the porous medium 12. Generally speaking, the measurement electronics 11 can include a signal generator module (not shown) and a signal processor module (not shown) whose operation will be described in more detail hereafter. In the situation where a plurality of sensors 15 are used, the measurement electronics 11 can also include a signal multiplexer module (not shown) which generally allows the signal generator and signal processor modules to be time-shared amongst each of the sensors.

1.2 Stacked Sensor

Figure 2:
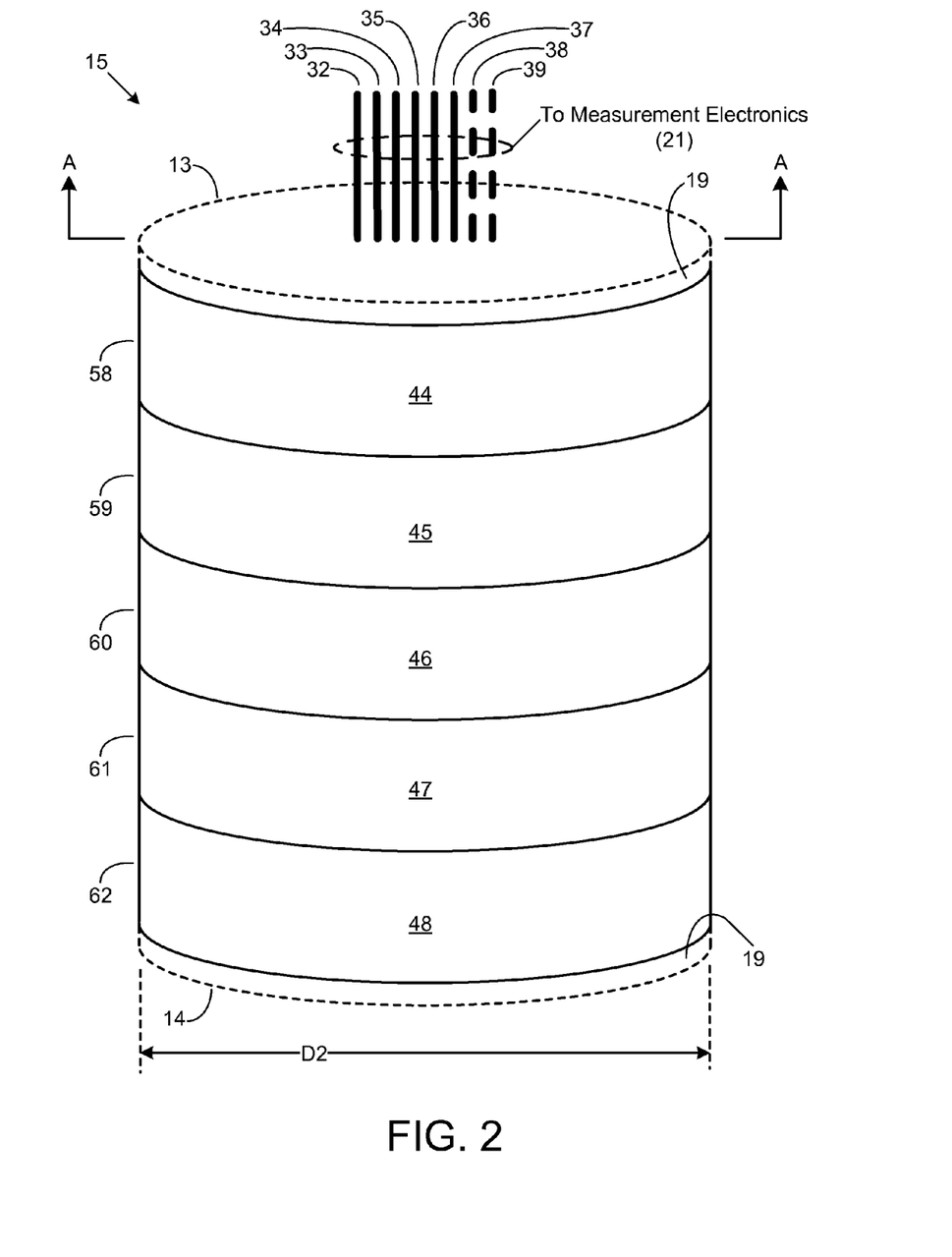
FIG. 2 is a diagram illustrating a longitudinal perspective view, in simplified form, of one embodiment of the stacked sensor.
Figure 3:
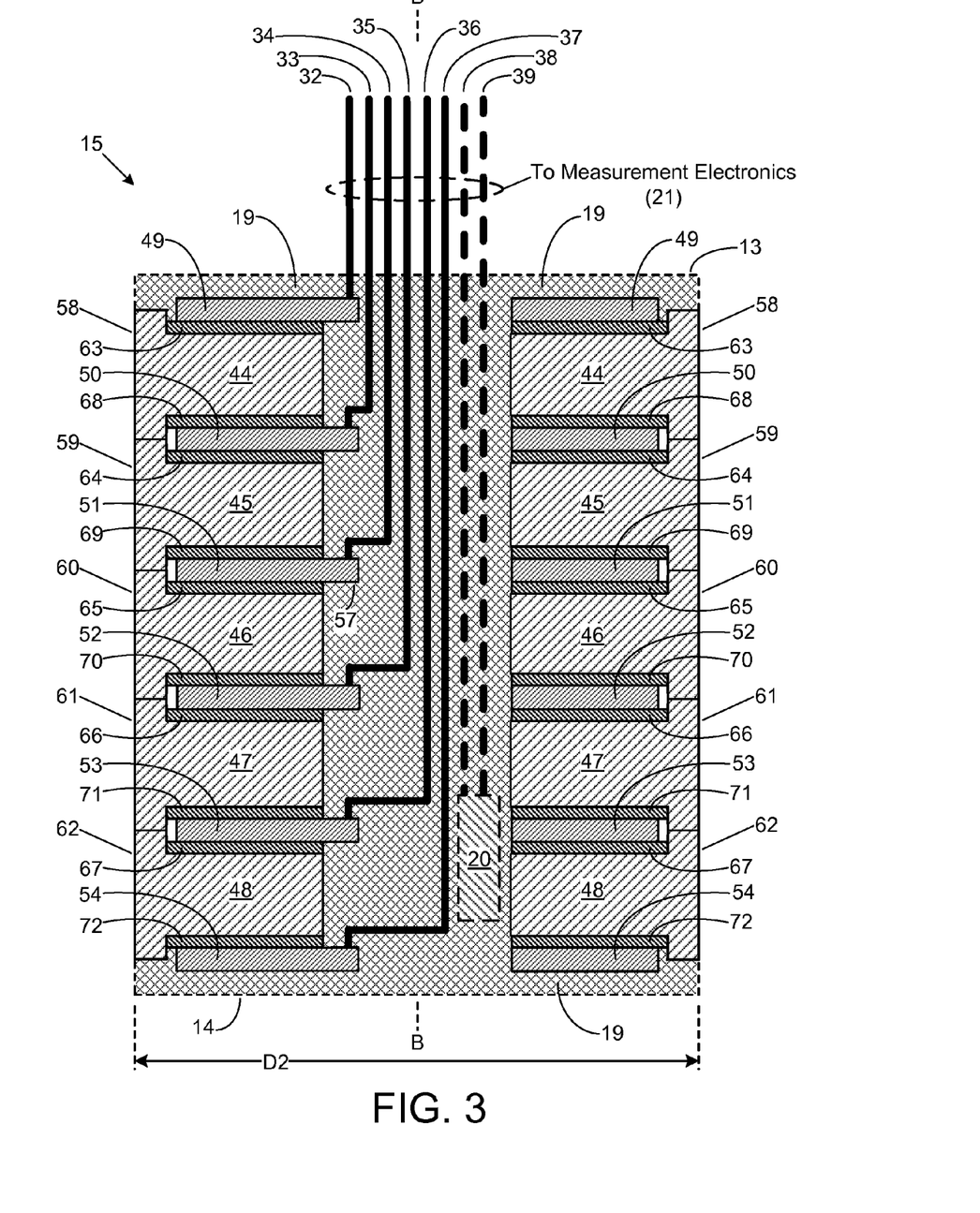
FIG. 3 is a diagram illustrating a cross-sectional view, in simplified form, of the stacked sensor of FIG. 2 taken along line A-A of FIG. 2.
Figures 4, 8:
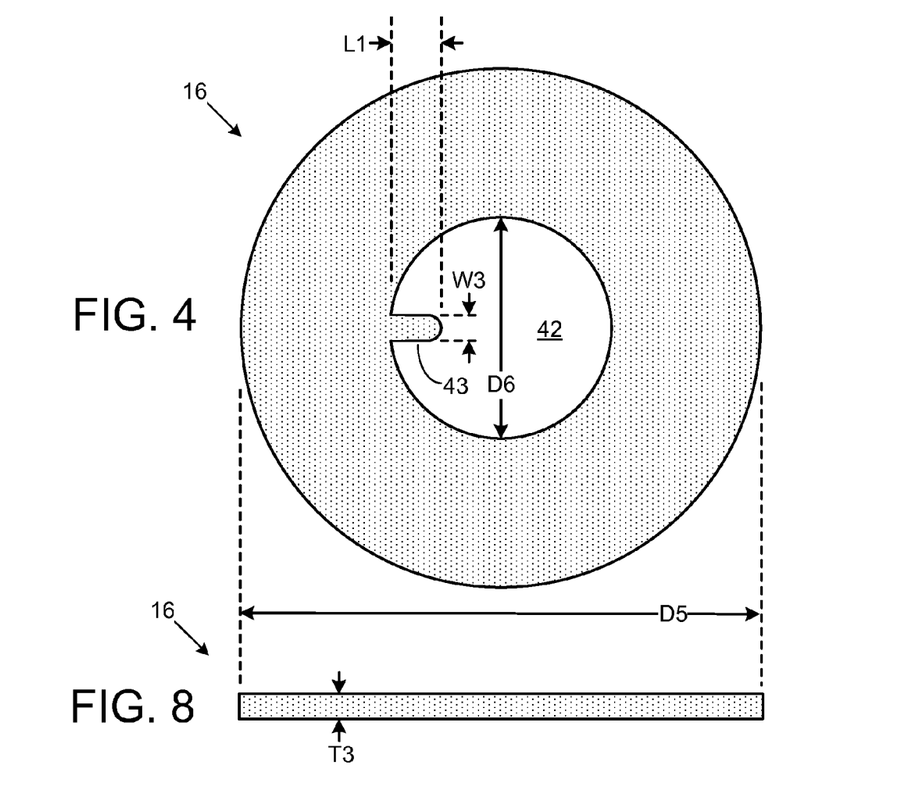
FIG. 4 is a diagram illustrating a standalone top view, in simplified form, of one embodiment of one of the electrically conductive interface plates included within the stacked sensor of FIG. 2.
FIG. 8 is a diagram illustrating a side view, in simplified form, of the electrically conductive interface plate of FIG. 4.
Figure 5:
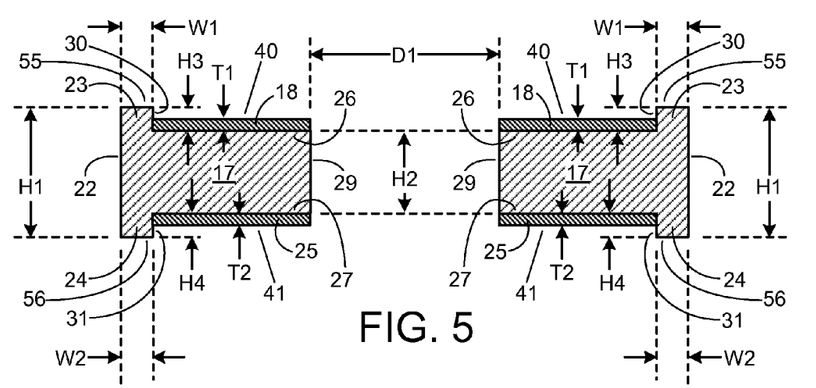
FIG. 5 is a diagram illustrating a standalone cross-sectional view, in simplified form, of an exemplary embodiment of one of the porous ceramic elements included within the stacked sensor of FIG. 2 taken along line A-A of FIG. 2.
Figure 6:
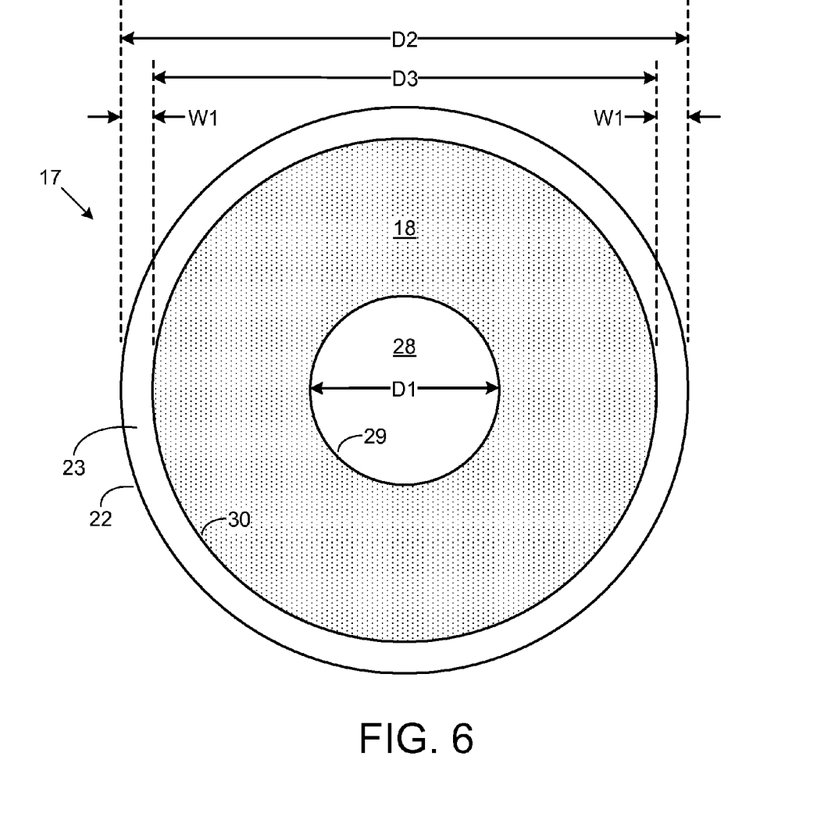
FIG. 6 is a diagram illustrating a top view, in simplified form, of the porous ceramic element of FIG. 5.
Figure 7:
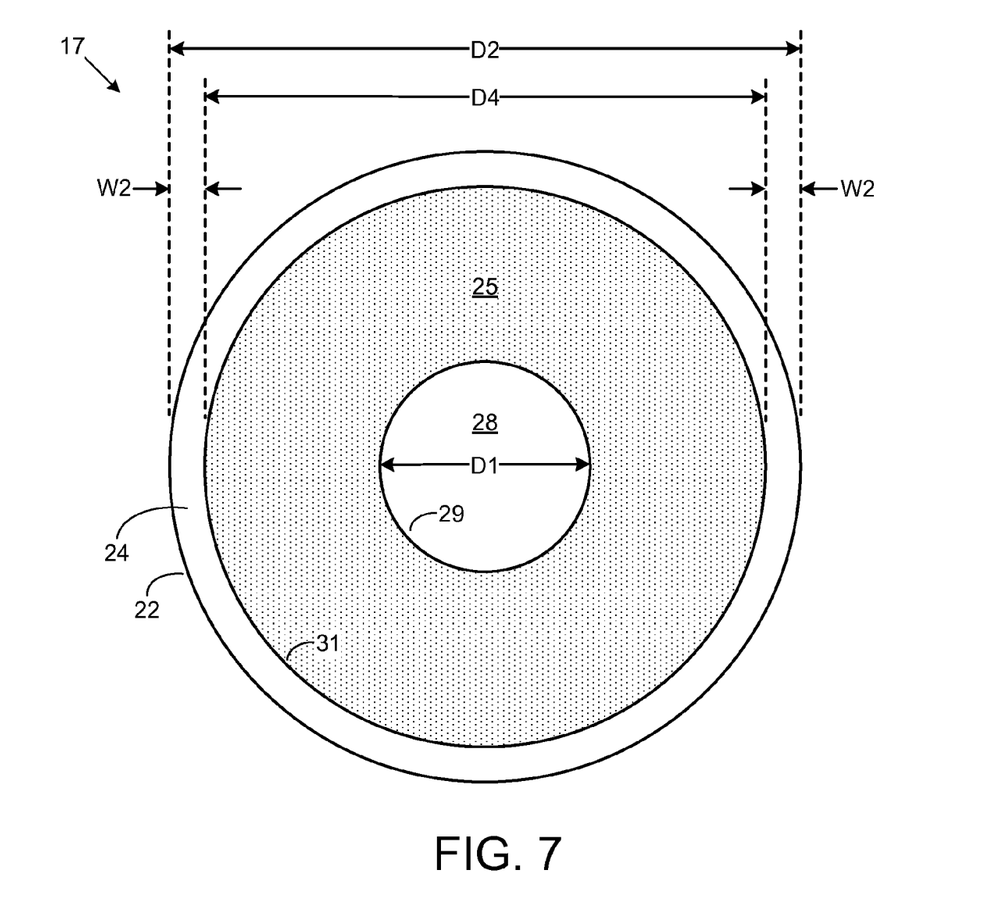
FIG. 7 is a diagram illustrating a bottom view, in simplified form, of the porous ceramic element of FIG. 5.

FIGS. 2-8 illustrate one embodiment, in simplified form, of the aforementioned stacked sensor. More particularly, FIG. 2 illustrates a longitudinal perspective view of the sensor. FIG. 3 illustrates a cross-sectional view of the sensor of FIG. 2 taken along line A-A of FIG. 2. FIG. 4 illustrates a standalone top view of one embodiment of one of the electrically conductive interface plates included within the sensor. FIG. 5 illustrates a standalone cross-sectional view of an exemplary embodiment of one of the porous ceramic elements included within the sensor taken along line A-A of FIG. 2. FIG. 6 illustrates a top view of the ceramic element of FIG. 5. FIG. 7 illustrates a bottom view of the ceramic element of FIG. 5. FIG. 8 illustrates a side view of the interface plate of FIG. 4.

As exemplified in FIGS. 1, 2 and 3, the stacked sensor 15 includes a plurality of porous ceramic elements 44-48, each having a common prescribed exterior diameter D2 and also having a radially outer vertical edge 58-62 which is exposed to the porous medium being tested 12. These vertical edges 58-62 thus allow each of the ceramic elements 44-48 to maintain fluid contact with the medium being tested 12. Accordingly and as will be described in more detail hereafter, each of the ceramic elements provides a means for absorbing a liquid from the medium being tested 12. The ceramic elements 44-48 are stacked one on top of another such that the radial axis of each of the ceramic elements is positioned along a common axis B-B, therefore forming a stack of two or more ceramic elements. It will thus be appreciated that the sensor includes one or more adjoining pairs of ceramic elements. By way of clarification, in the stacked sensor embodiment exemplified in FIGS. 2 and 3 where the sensor 15 includes five ceramic elements 44-48, the sensor also includes four adjoining pairs of ceramic elements (44 and 45, 45 and 46, 46 and 47, and 47 and 48).

As exemplified in FIGS. 5-7, each of the porous ceramic elements 17 includes a first axial opening 28 which is generally centered along the radial axis of the ceramic element, and which has a prescribed diameter D1. Each of the ceramic elements 17 also includes a top horizontal surface 26, a bottom horizontal surface 27, and a prescribed interior height H2 which is the distance between these top and bottom horizontal surfaces. Each of the ceramic elements 17 also includes an upwardly-facing raised rim 23 which is positioned on the top horizontal surface 26 of the ceramic element, and a downwardly-facing raised rim 24 which is positioned on the bottom horizontal surface 27 of the ceramic element. In an exemplary embodiment of the stacked sensor described herein, both the upwardly-facing and downwardly-facing raised rims 23 and 24 are positioned along the radially outer vertical edge 22 of each of the ceramic elements 17. The upwardly-facing raised rim 23 has a prescribed radial width W1 and extends upward a prescribed distance H3 from this top horizontal surface 26. Thus, the upwardly-facing rim 23 forms an axially-recessed cavity 40 on the top of each of the ceramic elements 17, where this cavity has a diameter D3 which equals the diameter D2 minus twice the width W1. The downwardly-facing raised rim 24 has a prescribed radial width W2 and extends downward a prescribed distance H4 from this bottom horizontal surface 27. Thus, the downwardly-facing rim 24 forms another axially-recessed cavity 41 on the bottom of each of the ceramic elements 17, where this cavity has a diameter D4 which equals the diameter D2 minus twice the width W2.

Referring again to FIGS. 5-7, in an exemplary embodiment of the stacked sensor described herein, radial widths W1 and W2 have the same value. Alternate embodiments of the stacked sensor are also possible where either width W1 is greater than width W2, or width W1 is less than width W2. Similarly, in an exemplary embodiment of the stacked sensor distances H3 and H4 have the same value. Alternate embodiments of the stacked sensor are also possible where either distance H3 is greater than distance H4, or distance H3 is less than distance H4. Each of the porous ceramic elements 17 has a prescribed exterior height H1 which equals the interior height H2 plus the distance H3 plus the distance H4. In one embodiment of the stacked sensor the interior heights H2 of each of the ceramic elements 17 have the same value. In another embodiment of the stacked sensor the interior heights H2 of each of the ceramic elements 17 have different values.

In the particular stacked sensor embodiment exemplified in FIGS. 2 and 3, the sensor 15 includes five ceramic elements 44-48. Alternate embodiments of the stacked sensor (not shown) are also possible where the sensor can include either less than five ceramic elements or greater than five ceramic elements.

Generally speaking and as exemplified in FIG. 3, each of the ceramic elements 44-48 also includes an upper electrically conductive coating 63-67 and a lower electrically conductive coating 68-72. More particularly and as exemplified in FIGS. 5-7, the upper electrically conductive coating 18 has a prescribed thickness T1 and is evenly applied onto the top horizontal surface 26 of each of the ceramic elements 17. The upper electrically conductive coating 18 generally extends from the radially inner vertical edge 29 of the ceramic element to the radially inner vertical edge 30 of the upwardly-facing raised rim 23. The lower electrically conductive coating 25 has a prescribed thickness T2 and is evenly applied onto the bottom horizontal surface 27 of each of the ceramic elements 17. The lower electrically conductive coating 25 generally extends from the radially inner vertical edge 29 of the ceramic element to the radially inner vertical edge 31 of the downwardly-facing raised rim 24. In an exemplary embodiment of the stacked sensor described herein, thicknesses T1 and T2 have the same value. Alternate embodiments of the stacked sensor are also possible where either thickness T1 can be greater than thickness T2, or thickness T1 can be less than thickness T2. The coatings 18 and 25 can be applied onto the top and bottom horizontal surfaces 26 and 27 using various methods such as a sputtering method, or a pad printing method, among others. Various types of materials can be employed for the coatings 18 and 25 such as an electrically conductive epoxy, among others.

Referring again to FIG. 3, each of the porous ceramic elements 44-48 serves as a dielectric between the upper and lower electrically conductive coatings 63-67 and 68-72 that are applied to the ceramic element. Furthermore, each of the ceramic elements 44-48 has a continuous, interconnected system of pores (not shown) which is permeable to liquids, gasses and various combinations thereof. Yet furthermore, the pores in each of the ceramic elements 44-48 have a known distribution throughout the ceramic element, and a known size distribution which is different than that of the other ceramic elements. Thus, each of the ceramic elements 44-48 exhibits a different known liquid-release curve (also known in the arts of hydrology and soil science as a "moisture-release curve" or a "moisture-retention curve"). Since the radially outer vertical edges 58-62 of the ceramic elements 44-48 are exposed to the porous medium being tested, liquids, gasses and various combinations thereof which may be present in the medium can flow into (or out of) the ceramic elements through these vertical edges. As is appreciated in the hydrology and soil science arts, the liquid-release curve of a material defines the relationship between the liquid content and the matric liquid potential of the material. It will further be appreciated that as the liquid content changes within each of the ceramic elements 44-48, the effective capacitance of the ceramic element will change. In other words, the ratio of liquid to air within the pores of each of the ceramic elements 44-48 generally determines the effective capacitance of the ceramic element. Given the foregoing, it will yet further be appreciated that each of the ceramic elements 44-48 operates as a discrete variable capacitor having an effective capacitance that is different from that of the other ceramic elements.

Referring again to FIGS. 1-3, since the radially outer vertical edges 58-62 of each of the porous ceramic elements 44-48 are exposed to the porous medium being tested 12, each of the ceramic elements maintains fluid contact with the medium. This allows for fast equalization of the liquid content within the medium being tested 12 and the liquid content within each of the ceramic elements 44-48, and also allows this equalization to be continuously maintained as the liquid content within the medium changes. In other words, when a previously unused stacked sensor 15 (e.g., a sensor whose ceramic elements 44-48 are dry) is disposed in the medium 12 for the first time, any liquid which is present in the medium can flow from the medium and be absorbed into each of the ceramic elements until the liquid content within the medium and that within each of the ceramic elements are equalized. Then, if the liquid content of the medium 12 increases, additional liquid can flow from the medium and be absorbed into each of the ceramic elements 44-48 until the liquid content within the medium and that within each of the ceramic elements are re-equalized. Likewise, if the liquid content of the medium 12 decreases, liquid can flow from each of the ceramic elements 44-48 and be absorbed back into the medium until the liquid content within the medium and that within each of the ceramic elements are re-equalized. Given the foregoing, it will be appreciated that the effective capacitance of each of the ceramic elements 44-48 changes in conjunction with changes in the amount of liquid which is present within the medium 12.

Using porous ceramic elements as a dielectric in the stacked sensor embodiments described herein is advantageous for a variety of reasons including, but not limited to, the following. The ceramic elements are naturally hydrophilic. Thus, a polar liquid from the surrounding porous medium being tested is "wicked" into the pores of the ceramic elements by capillary action. In other words and generally speaking, the liquid is naturally pulled from the medium being tested and flows into the pores of the ceramic elements (or is pulled from the pores of the ceramic elements and flows back into the medium being tested as the case may be) until the aforementioned equalization is achieved. The ceramic elements can be mass produced with very consistent and uniform pore structures throughout each of the elements thus making the aforementioned precise measurements possible. The ceramic elements are very durable and generally inert. Thus, the ceramic elements will not degrade or change their porosity properties when salt or other minerals or chemicals are present in the medium being tested.

Referring again to FIGS. 2 and 3, since the pores in each of the porous ceramic elements 44-48 have a different known liquid-release curve, when the stacked sensor 15 is exposed to the liquid content within the porous medium being tested different amounts of liquid will be absorbed into the different ceramic elements. As a result, the different ceramic elements 44-48 will develope different effective capacitances. As is appreciated in the art of porous ceramics, the pore structure of a given ceramic element can be specified in terms of an air entry value (which is commonly measured using a unit of pressure known as a "bar") and a flow rate.

In the stacked sensor embodiment exemplified in FIGS. 2 and 3 where the sensor 15 includes five porous ceramic elements 44-48, the following are exemplary pore structures which can be employed for each of the ceramic elements. The topmost ceramic element 44 in the stack of two or more ceramic elements can have a ½ bar high flow pore structure. A first intervening ceramic element 45 which is immediately beneath the topmost ceramic element 44 in the stack can have a 1 bar high flow pore structure. A second intervening ceramic element 46 which is immediately beneath the first intervening ceramic element 45 in the stack can have a 2 bar high flow pore structure. A third intervening ceramic element 47 which is immediately beneath the second intervening ceramic element 46 in the stack can have a 5 bar high flow pore structure. The bottommost ceramic element 48 which is immediately beneath the third intervening ceramic element 47 in the stack can have a 15 bar high flow pore structure. Various other bar values and flow rates can be employed for the different ceramic elements in the stack. Additionally, rather than the bar values being distributed in a downwardly increasing manner through the stack as just described, the bar values can be distributed through the stack in various other ways such as a downwardly decreasing manner, among others.

As exemplified in FIG. 3, the stacked sensor 15 also generally includes a first number of electrically conductive interface plates 49-54, where this first number is one greater than the total quantity of porous ceramic elements 44-48 that are included within the sensor (e.g., in the aforementioned stacked sensor embodiment where the sensor includes five ceramic elements, the sensor will also include six interface plates). More particularly, the sensor includes a topmost interface plate 49, one or more intervening interface plates 50-53, and a bottommost interface plate 54. As exemplified in FIGS. 4 and 8, and referring again to FIGS. 6 and 7, each of the interface plates 16 has a prescribed exterior diameter D5 and a prescribed thickness T3. Each of the interface plates 16 includes a second axial opening 42 which is generally centered along the radial axis of the interface plate. The second axial opening 42 has a prescribed diameter D6 which is generally less than or equal to the diameter D1 of the first axial opening 28 of each of the sensor's ceramic elements 17. Each of the interface plates 16 also includes a tab 43 which protrudes radially inward toward the center of the second axial opening 42. The tab has a prescribed length L1 and a prescribed width W3. A variety of sizes can be employed for length L1 and width W3. In an exemplary embodiment of the stacked sensor described herein length L1 can be 0.028 inches and width W3 can be 0.032 inches.

Generally speaking and referring again to FIG. 3, the first number of electrically conductive interface plates 49-54 are axially distributed within the stacked sensor 15 such that the radial axis of each of the interface plates is positioned along the common axis B-B, and each of the porous ceramic elements 44-48 is sandwiched between a different pair of interface plates such that substantial electrical contact is established between the ceramic element and both plates in the pair. In other words, the first number of interface plates 49-54 serves as a planar conductive means for electrically contacting the plurality of ceramic elements 44-48 within the sensor. More particularly and as exemplified in FIG. 3, the topmost interface plate 49 is disposed onto the upper electrically conductive coating 63 on the upper ceramic element 44 in the topmost adjoining pair of ceramic elements 44 and 45 in the stack. Each of the intervening interface plates 50-53 is disposed between a different adjoining pair of ceramic elements in the stack (44 and 45, 45 and 46, 46 and 47, and 47 and 48) such that the intervening interface plate (e.g., plate 50) is sandwiched between the lower electrically conductive coating on the upper ceramic element in the adjoining pair (e.g., coating 68 on element 44 in the pair 44 and 45) and the upper electrically conductive coating on the lower ceramic element in the adjoining pair (e.g., coating 64 on element 45 in the pair 44 and 45). The bottommost interface plate 54 is disposed onto the lower electrically conductive coating 72 on the lower ceramic element 48 in the bottommost adjoining pair of ceramic elements 47 and 48 in the stack. As exemplified in FIG. 3, the first axial openings of the ceramic elements 44-48 combine with the second axial openings of the interface plates 49-54 to form a longitudinal cavity within the sensor 15, where this longitudinal cavity is centered along the common axis B-B and extends from the proximal end 13 of the sensor to the distal end 14 of the sensor.

Referring again to FIGS. 4-8, the exterior diameter D5 of each of the electrically conductive interface plates 16 is set to be less than the diameter D3 of the axially-recessed cavity 40 on the top of each of the porous ceramic elements 17, and also less than the diameter D4 of the axially-recessed cavity 41 on the bottom of each of the ceramic elements 17. Additionally, the aforementioned distances H3 and H4, and thicknesses T1, T2 and T3 are interrelated as follows. Values are selected for distances H3 and H4, and for thicknesses T1, T2 and T3, such that the sum of thicknesses T1, T2 and T3 equals the sum of distances H3 and H4. Thus, as exemplified in FIG. 3, substantial electrical contact is established between the topmost interface plate 49 and the upper electrically conductive coating 63 on the topmost ceramic element 44 in the stack. Substantial electrical contact is also established between each of the intervening interface plates (e.g., plate 50) and both the lower electrically conductive coating on the upper ceramic element (e.g., coating 68 on element 44) in the adjoining pair of ceramic elements between which the intervening interface plate is disposed, and the upper electrically conductive coating on the lower ceramic element (e.g., coating 64 on element 45) in this adjoining pair of ceramic elements. Substantial electrical contact is also established between the bottommost interface plate 54 and the lower electrically conductive coating 72 on the bottommost ceramic element 48 in the stack. Finally, the bottom edge 56 of the downwardly-facing raised rim 24 of the upper ceramic element in each of the adjoining pairs of ceramic elements in the stack (e.g., element 44) contacts the top edge 55 of the upwardly-facing raised rim 23 of the lower ceramic element in this adjoining pair (e.g., element 45).

Referring again to FIGS. 4 and 5, it is noted that the following additional considerations exist when selecting the particular values that are used for the exterior diameter D5 of each of the electrically conductive interface plates 16 and the diameter D6 of the second axial opening 42 of each of the interface plates. On one hand, larger values for diameter D5 and smaller values for diameter D6 for a given interface plate will increase the surface area of the plate that contacts the upper and/or lower electrically conductive coatings 18 and/or 25 on the ceramic element(s) 17 either between which the plate is sandwiched, or onto which the plate is disposed as described heretofore. This generally enhances the precision of the measurements being made by the stacked sensor. On the other hand, smaller values for diameter D5 and larger values for diameter D6 for a given interface plate will decrease the surface area of the plate that contacts the upper and/or lower electrically conductive coatings on the ceramic element(s) either between which the plate is sandwiched, or onto which the plate is disposed. This generally speeds up the response time of the sensor when making measurements in the porous medium, which can be advantageous in certain applications. It is further noted that the diameters D5 and/or D6 can be individually selected for each of the interface plates (e.g., different plates within the sensor can employ different values for diameters D5 and/or D6). Doing this can be advantageous since it allows the effective capacitance and the response time of each of the ceramic elements within the sensor to be balanced.

Referring again to FIGS. 3 and 4, the stacked sensor 15 also generally includes a second number of electrical conductors 32-37, where this second number equals the aforementioned first number (e.g., in the aforementioned stacked sensor embodiment where the sensor includes six electrically conductive interface plates 49-54, the sensor will also include six of these electrical conductors). As exemplified in FIG. 3, a distal end of each of the electrical conductors 32-37 is electrically attached to a different one of the interface plates 49-54. In an exemplary embodiment of the stacked sensor described herein the electrical conductors 32-37 can be wires, and the distal end of each of the wires can be electrically attached (e.g., soldered, among other ways) to the tab 43 on a different one of the interface plates (e.g., the distal end of the wire associated with conductor 34 can be electrically attached to the tab 57 on interface plate 51). As further exemplified in FIG. 3, a proximal end of each of the electrical conductors 32-37 is routed through the longitudinal cavity within the sensor 15 to the proximal end 13 of the sensor. Given the foregoing, it will be appreciated that the second number of electrical conductors 32-37 serves as an elongated conductive means for propagating an electrical signal from a proximal end 13 of the sensor 15 to the first number of interface plates 49-54 within the sensor.

In the stacked sensor embodiment exemplified in FIGS. 2 and 3, the proximal end of each of the electrical conductors 32-37 exits the longitudinal cavity at the proximal end 13 of the sensor 15 such that each of the conductors is exposed, thus enabling their connection to the measurement electronics. In an alternate embodiment of the stacked sensor (not shown) the proximal end of each of the electrical conductors can be electrically attached to a connector which is located at the proximal end of the sensor.

Referring again to FIG. 3, the first number of electrically conductive interface plates 49-54 can be constructed from any material which is electrically conductive. By way of example but not limitation, the interface plates can be constructed from a variety of different metals such as copper, brass, stainless steel, a nickel alloy, aluminum, gold, platinum, silver, or the like. The interface plates can also be constructed by sintering a powdered form of these metals. The interface plates can also be formed as a composite material using vapor deposition, liquid deposition, or flame deposition of any of these metals on top of a non-conductive material. Each of the interface plates can either be constructed from the same material, or they can be constructed from different materials.

In the stacked sensor embodiment exemplified in FIGS. 2, 6 and 7, each of the porous ceramic elements 17 has a radially exterior shape that is circular. The first axial opening 28 of each of the ceramic elements has a radial shape that is also circular. A variety of alternate embodiments of each of the ceramic elements (not shown) are also possible. By way of example but not limitation, rather than having a radially exterior shape that is circular, each of the ceramic elements can also have any other radially exterior shape. Thus, each of the ceramic elements can have a radially exterior shape that is oval, triangular, square, rectangular, pentagonal, hexagonal or octagonal, among others. Furthermore, rather than the first axial opening of each of the ceramic elements having a radial shape that is circular, the first axial opening of each of the ceramic elements can also have any other radial shape. Thus, the first axial opening of each of the ceramic elements can have a radial shape that is oval, triangular, square, rectangular, pentagonal, hexagonal or octagonal, among others.

In the stacked sensor embodiment exemplified in FIGS. 2, 6 and 7, the radial shape of the first axial opening 28 of each of the porous ceramic elements 17 is the same as the radially exterior shape of the ceramic element (i.e., the radial shape of each ceramic element's first axial opening and the ceramic element's radially exterior shape are both circular). A variety of alternate embodiments of the stacked sensor (not shown) are also possible where the radial shape of the first axial opening of each ceramic element and the radially exterior shape of the ceramic element are different. By way of example but not limitation, the radially exterior shape of each of the ceramic elements can be circular and the first axial opening of each of the ceramic elements can have a radial shape that is square, or vice versa. The radially exterior shape of each of the ceramic elements can be oval and the first axial opening of each of the ceramic elements can have a radial shape that is rectangular, or vice versa. The radially exterior shape of each of the ceramic elements can be triangular and the first axial opening of each of the ceramic elements can have a radial shape that is octagonal, or vice versa.

In the stacked sensor embodiment exemplified in FIGS. 2, 4, 6 and 7 each of the electrically conductive interface plates 16 has a radially exterior shape that is the same as the radially exterior shape of each of the porous ceramic elements 17 (e.g., the radially exterior shape of each of the interface plates and each of the ceramic elements is circular). Furthermore, the second axial opening 42 of each of the interface plates has a radial shape that is the same as the radial shape of the first axial opening 28 of each of the ceramic elements (e.g., the radial shape of the second axial opening of each of the interface plates and each of the ceramic elements is also circular). A variety of alternate embodiments of each of the interface plates (not shown) are also possible. By way of example but not limitation, rather than having a radially exterior shape that is the same as the radially exterior shape of each of the ceramic elements, each of the interface plates can also have a radially exterior shape that is different than the radially exterior shape of each of the ceramic elements, where the different radially exterior shape of each of the interface plates can be any of the aforementioned shapes. Additionally, rather than the second axial opening of each of the interface plates having a radial shape that is the same as the radial shape of the first axial opening of each of the ceramic elements, the second axial opening of each of the interface plates can also have a radial shape that is different than the radial shape of the first axial opening of each of the ceramic elements, where the different radial shape of the second axial opening of each of the interface plates can be any of the aforementioned shapes.

Referring again to FIGS. 2 and 3, the stacked sensor 15 can optionally be potted as follows in order to maximize the sensor's operating lifetime, reliability and resistance to shock and vibration. A potting compound 19 can be applied to the sensor 15 such that the compound fills the longitudinal cavity within the sensor, covers the distal end 14 of the sensor, and also covers the proximal end 13 of the sensor. Various materials can be employed for the potting compound 19 including, but not limited to, an electrically non-conductive epoxy.

As exemplified in FIG. 3, the stacked sensor 15 can optionally also include a temperature sensing device 20 which can serve as a means for measuring the temperature of the porous medium being tested. Various types of devices can be employed for the temperature sensing device 20 such as a thermistor or a thermocouple, among others. Whenever the sensor 15 includes the temperature sensing device 20, a distal end of the aforementioned additional pair of electrical conductors 38 and 39 is electrically attached to this device. A proximal end of the additional pair of electrical conductors 38 and 39 is routed through the longitudinal cavity within the sensor 15 to the proximal end 13 of the sensor. In the stacked sensor embodiment exemplified in FIGS. 2 and 3, the proximal end of the additional pair of electrical conductors 38 and 39 exits the longitudinal cavity at the proximal end 13 of the sensor 15 such that the conductors are exposed, thus enabling their connection to the measurement electronics. In an alternate embodiment of the stacked sensor (not shown) this proximal end of the additional pair of electrical conductors can be electrically attached to the aforementioned connector which is located at the proximal end of the sensor.

Generally speaking and referring again to FIG. 3, the temperature sensing device 20 can be located in various places within the stacked sensor 15. By way of example but not limitation, in one embodiment of the stacked sensor described herein the temperature sensing device 20 can be located in the longitudinal cavity within the sensor 15 near the distal end 14 of the sensor as exemplified in FIG. 3. Alternate embodiments of the stacked sensor (not shown) are also possible where the temperature sensing device can be located in any other part of the longitudinal cavity.

Referring again to FIGS. 1 and 3, in addition to the temperature sensing device 20, the stacked sensor 15 may optionally also include other electronic components (not shown) which can be located in various places within the sensor such as the aforementioned places, among others. Examples of such other electronic components include, but are not limited to, the following. In a situation where the sensor 15 is remotely located from the measurement electronics 11, the other electronic components may include a third number of signal buffers (not shown) and a power source (not shown, such as a battery, or the like) for powering the buffers. The third number equals the first number (i.e., the number of signal buffers equals the number of electrically conductive interface plates 49-54). Each of the buffers can be electrically connected in series with a different one of the second number of electrical conductors 32-37. In this situation, if the sensor 15 also includes the temperature sensing device 20, the other electronic components may also include an additional pair of signal buffers (not shown) which can be electrically connected in series with the additional pair of electrical conductors 38 and 39. In another situation where the sensor 15 is even more remotely located from the measurement electronics 11, the other electronics may also include analog-to-digital (A/D) converter and digital signal processing (DSP) electronics (not shown), along with a power source (not shown, such as a battery, or the like) for powering these electronics. It will be appreciated that the A/D converter and DSP electronics can be used to perform front-end processing of the electrical signals on the various conductors 32-39 during the testing of the porous medium.

Referring again to FIGS. 4-8, a variety of sizes can be employed for the diameter D1 of the first axial opening 28 of each of the porous ceramic elements 17, the exterior diameter D2 of each of the ceramic elements, the radial widths W1 and W2 of the upwardly-facing and downwardly-facing raised rims 23 and 24 of each of the ceramic elements, the interior height H2 of each of the ceramic elements, the thicknesses T1 and T1 of the first and second coatings 18 and 25 on each of the ceramic elements, the distances H3 and H4 the upwardly-facing and downwardly-facing raised rims 23 and 24 extend from the top and bottom surfaces 26 and 27 of each of the ceramic elements, the exterior diameter D5 of each of the electrically conductive interface plates 16, the diameter D6 of the second axial opening 42 of each of the interface plates, and the thickness T3 of each of the interface plates. The interrelationship between diameter D5, diameter D2 and width W1 has been described heretofore. The interrelationship between diameter D5, diameter D2 and width W2 has also been described heretofore. The interrelationship between distance H3, distance H4, thickness T1, thickness T2 and thickness T3 has also been described heretofore. Generally speaking, the size of diameters D1, D2, D5 and D6, radial widths W1 and W2, and height H2 for a given sensor can be tailored to factors such as the particular type of porous medium being tested, the particular dielectric influences in the medium and/or characteristics of the medium which are being measured, and the particular manner in which the testing is performed (e.g., whether the medium is being tested in situ or a sample of the medium is being tested in a different setting such as a laboratory environment or the like). In an exemplary embodiment of the stacked sensor described herein where a medium such as soil is being tested in situ, and where each of the ceramic elements has a radial cross-sectional shape that is circular and each of the interface plates has a radial cross-sectional shape that is circular, diameter D1 can be 0.187 inches, diameter D2 can be 0.500 inches, width W1 can be 0.030 inches, width W2 can be 0.030 inches, height H2 can be 0.070 inches, thickness T1 can be 0.0035 inches, thickness T2 can be 0.0035 inches, distance H3 can be 0.006 inches, distance H4 can be 0.006 inches, diameter D5 can be 0.434 inches, diameter D6 can be 0.0.187 inches, and thickness T3 can be 0.005 inches.

1.3 Making Measurements in the Porous Medium

As described heretofore, the stacked sensor embodiments described herein can measure one or more dielectric influences in the porous medium, such as the volumetric liquid content of the medium and the salinity of the medium, among other things. The stacked sensor embodiments can also measure one or more characteristics of the medium, such as the temperature of the medium, the fluid holding capabilities of the medium, and other detectable physical or chemical properties of the medium. This section provides a general overview of exemplary ways in which the measurement electronics can interoperate with a given sensor to make these measurements in the medium.

In one embodiment of the stacked sensor described herein the signal generator module of the measurement electronics can apply an alternating current (AC) voltage to each of the sensor's porous ceramic elements. The signal processor module of the measurement electronics can then measure the complex impedance of each of the sensor's ceramic elements. By way of clarification and referring again to FIG. 3, it will be appreciated that the signal generator module can apply the AC voltage (not shown) to a particular ceramic element by inputting the AC voltage into the particular pair of electrical conductors (e.g., conductors 35 and 36) that are electrically attached to the particular pair of electrically conductive interface plates (e.g., plates 52 and 53) that substantially contact the upper and lower electrically conductive coatings (e.g., coatings 66 and 71) on the particular ceramic element (e.g., element 47). Similarly, the signal processor module can measure the complex impedance of the particular ceramic element using this same particular pair of electrical conductors.

It is noted that the AC voltage either can have a prescribed fixed frequency, or can be varied (e.g., swept) over a prescribed range of frequencies in order to measure changes in the frequency-dependent characteristics of each of the sensor's porous ceramic elements. It is also noted that the AC voltage can be applied to each of the ceramic elements, and the complex impedance thereof can be measured, either for each of the ceramic elements independently, or for all the ceramic elements in unison, or for prescribed pairs of ceramic elements. Additionally, the complex impedance of each of the ceramic elements can be measured either at a single point in time or over a prescribed period of time.

Generally speaking and as is appreciated in the art of electronics, the complex impedance of each of the stacked sensor's porous ceramic elements has both an amplitude component and a phase component. The amplitude of the complex impedance is the ratio of the voltage amplitude to the current amplitude. The phase of the complex impedance is the phase shift by which the current is ahead of the voltage. Any liquid content that is present in a given ceramic element will cause a phase shift in the complex impedance of the ceramic element. As described heretofore, since the pores in each of the sensor's ceramic elements have a different known liquid release curve, when the sensor is exposed to the liquid content within the porous medium being tested different amounts of liquid will be absorbed into each of the ceramic elements, resulting in the different ceramic elements developing different effective capacitances. As a result, the complex impedance of each of the ceramic elements will have a different phase shift. The signal processor module can analyze the complex impedance measurements in a variety of ways in order to compute this phase shift information along with other types of information. The volumetric liquid content of the medium and the fluid holding capabilities of the medium (among other things) can then be inferred from the computed phase shift information.

In another embodiment of the stacked sensor described herein the signal generator module can apply a direct current (DC) voltage to each of the sensor's porous ceramic elements, and the signal processor module can then measure the resistance of each of the ceramic elements, either for each ceramic element independently, or for all the ceramic elements in unison, or for prescribed pairs of ceramic elements. Additionally, the resistance of each of the ceramic elements can be measured either at a single point in time or over a prescribed period of time. Generally speaking and as is appreciated in the arts of hydrology and soil science, any salt which is present in the porous medium being tested will naturally be absorbed into a liquid which is present in the medium. Thus, as the salinity of the medium increases the salinity of the liquid within each of the ceramic elements will increase until equalization occurs there-between. Correspondingly, as the salinity of the medium decreases the salinity of the liquid within each of the ceramic elements will decrease until equalization occurs there-between. As the salinity of the liquid absorbed into each of the ceramic elements increases, the resistance of each of the ceramic elements generally decreases. The salinity of the medium (among other things) can be inferred from these resistance measurements.

In yet another embodiment of the stacked sensor described herein the signal generator module can apply a DC voltage to the temperature sensing device which can optionally be included within the sensor. The signal processor module can then measure the resistance of the temperature sensing device. By way of clarification and referring again to FIG. 3, it will be appreciated that the signal generator module can apply the DC voltage (not shown) to the temperature sensing device by inputting the DC voltage into the additional pair of electrical conductors 38 and 39 that is electrically attached to this device. Similarly, the signal processor module can measure the resistance of the temperature sensing device using the additional pair of electrical conductors. The temperature of the porous medium being tested can be inferred from this resistance measurement.

1.4 Stacked Sensor Having Interleaved Insulating Elements

Generally speaking, this section describes an alternate embodiment of the stacked sensor which includes non-porous and electrically non-conductive insulating elements (hereafter simply referred to as "insulating elements") that are interleaved between a plurality of porous ceramic elements in the sensor. These insulating elements serve to minimize the capacitive coupling that can occur between adjacent ceramic elements in the sensor. This particular embodiment of the stacked sensor is hereafter referred to as the "interleaved insulator sensor." The interleaved insulator sensor is advantageous in situations where the measurements being made by the sensor are sensitive to capacitive coupling between adjacent ceramic elements in the sensor.

Figure 10:
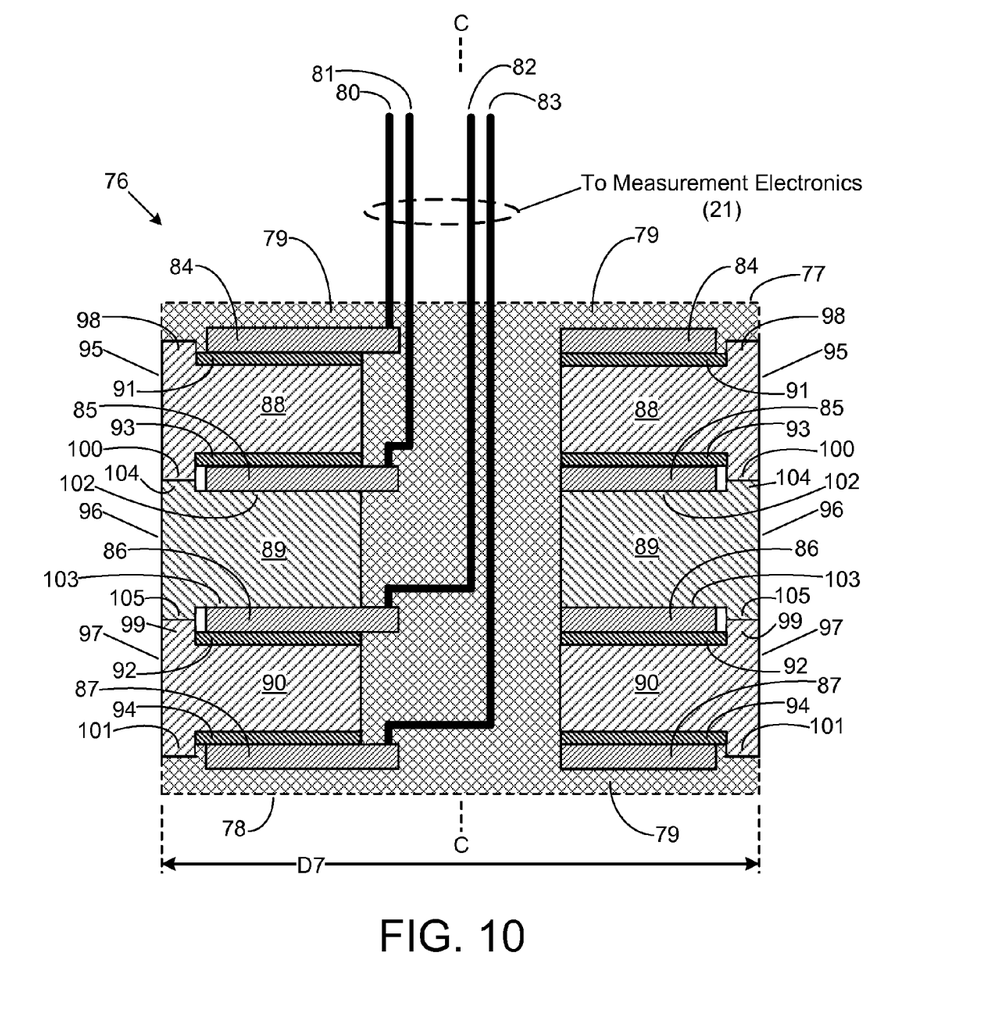
FIG. 10 is a diagram illustrating a cross-sectional view, in simplified form, of an alternate embodiment of the stacked sensor.
Figure 11:
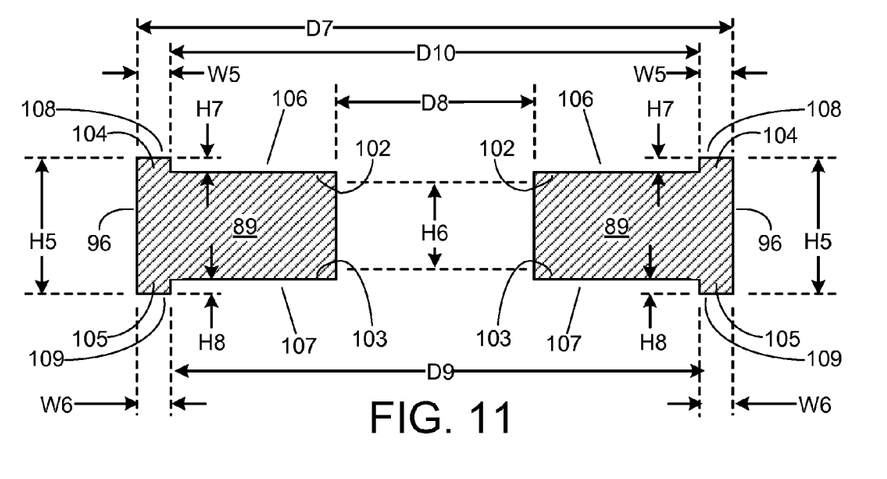
FIG. 11 is a diagram illustrating a standalone cross-sectional view, in simplified form, of an exemplary embodiment of a non-porous and electrically non-conductive insulating element included within the stacked sensor of FIG. 10.

FIG. 10 illustrates a cross-sectional view, in simplified form, of an exemplary embodiment of the interleaved insulator sensor. FIG. 11 illustrates a standalone cross-sectional view, in simplified form, of an exemplary embodiment of the insulating element included within the sensor of FIG. 10. As exemplified in FIG. 10, the interleaved insulator sensor 76 includes a plurality of porous ceramic elements 88 and 90, each having a common prescribed exterior diameter D7 and also having a radially outer vertical edge 95 and 97 which is exposed to the porous medium being tested. These vertical edges 95 and 97 thus allow each of the ceramic elements 88 and 90 to maintain fluid contact with the medium being tested. The individual ceramic elements 88 and 90 have the same features and attributes as the ceramic elements described in section 1.2. In other words, each of the ceramic elements 88 and 90 includes a first axial opening which is generally centered along the radial axis of the ceramic element. Each of the ceramic elements 88 and 90 also includes a first top horizontal surface and a first upwardly-facing raised rim 98 and 99 which is positioned on this top horizontal surface and forms an axially-recessed cavity on the top of the ceramic element. Each of the ceramic elements 88 and 90 also includes a first bottom horizontal surface and a first downwardly-facing raised rim 100 and 101 which is positioned on this bottom horizontal surface and forms an axially-recessed cavity on the bottom of the ceramic element. Each of the ceramic elements 88 and 90 also includes an upper electrically conductive coating 91 and 92 and a lower electrically conductive coating 93 and 94. These coatings 91-94 have the same features and attributes as the electrically conductive coatings described in section 1.2.

As exemplified in FIGS. 10 and 11, the interleaved insulator sensor 76 also includes a first number of insulating elements 89, where this first number is one less than the total quantity of porous ceramic elements 88 and 90 that are included within the sensor. The insulating elements can be made of any material which is non-porous and electrically non-conductive. The radial axis of each of the insulating elements 89 and each of the ceramic elements 88 and 90 is positioned along a common axis C-C. The insulating elements 89 are interleaved between the ceramic elements 88 and 90 such that each insulating element is sandwiched between a different pair of ceramic elements, therefore forming a stack of two or more ceramic elements with one or more insulating elements interleaved there-between. In an exemplary embodiment of the interleaved insulator sensor 76 each of the insulating elements 89 has an exterior diameter which is approximately the same as the exterior diameter D7 of the porous ceramic elements 88 and 90. As such, the radially outer vertical edges 96 of the insulating elements 89 are generally vertically aligned with the radially outer vertical edges 95 and 97 of the ceramic elements 88 and 90. In an exemplary embodiment of the interleaved insulator sensor 76 the insulating elements 89 have a radially exterior shape that is the same as that of the ceramic elements 88 and 90.

As exemplified in FIGS. 10 and 11, each of the insulating elements 89 includes a second axial opening which is generally centered along the radial axis of the insulating element, and which has a prescribed diameter D8. In an exemplary embodiment of the interleaved insulator sensor 76 the second axial opening of each of the insulating elements 89 has a radial shape that is the same as the radially exterior shape of the insulating element, and diameter D8 is approximately the same as the aforementioned diameter D1 of the first axial openings of the porous ceramic elements 88 and 90. A variety of alternate embodiments of the interleaved insulator sensor (not shown) are also possible where the radial shape of the second axial opening of each insulating element and the radially exterior shape of the insulating element are different, and where diameter D8 is either greater than or less than diameter D1.

As exemplified in FIGS. 10 and 11, each of the insulating elements 89 also includes a second top horizontal surface 102, a second bottom horizontal surface 103, and a prescribed interior height H6 which is the distance between these top and bottom horizontal surfaces. Each of the insulating elements 89 also includes a second upwardly-facing raised rim 104 which is positioned on the top horizontal surface 102 of the insulating element, and a second downwardly-facing raised rim 105 which is positioned on the bottom horizontal surface 103 of the insulating element. In an exemplary embodiment of the interleaved insulator sensor 76 both the second upwardly-facing and second downwardly-facing raised rims 104 and 105 are positioned along the radially outer vertical edges 96 of the insulating elements 89.

As exemplified in FIG. 11, the second upwardly-facing raised rim 104 of each of the insulating elements 89 has a prescribed radial width W5 and extends upward a prescribed distance H7 from the top horizontal surface 102 of the insulating element. Thus, the second upwardly-facing raised rim 104 forms an axially-recessed cavity 106 on the top of each of the insulating elements 89, where this cavity has a diameter D10 which equals the diameter D7 minus twice the width W5. The second downwardly-facing raised rim 105 of each of the insulating elements 89 has a prescribed radial width W6 and extends downward a prescribed distance H8 from the bottom horizontal surface 103 of the insulating element. Thus, the second downwardly-facing raised rim 105 forms an axially-recessed cavity 107 on the bottom of each of the insulating elements 89, where this cavity has a diameter D9 which equals the diameter D7 minus twice the width W6.

As exemplified in FIG. 10 and referring again to FIG. 11, in an exemplary embodiment of the interleaved insulator sensor 76 width W5 is approximately the same as the aforementioned radial width W2 of the downwardly-facing raised rims 100 and 101 of the porous ceramic elements 88 and 90. Alternate embodiments of the interleaved insulator sensor (not shown) are also possible where either width W5 is greater than width W2, or width W5 is less than width W2. Similarly, in an exemplary embodiment of the interleaved insulator sensor 76 width W6 is approximately the same as the aforementioned radial width W1 of the upwardly-facing raised rims 98 and 99 of the ceramic elements 88 and 90. Alternate embodiments of the interleaved insulator sensor (not shown) are also possible where either width W6 is greater than width W1, or width W6 is less than width W1.

Referring again to FIG. 11, in an exemplary embodiment of the interleaved insulator sensor distances H7 and H8 have the same value. Alternate embodiments of the interleaved insulator sensor are also possible where either distance H7 is greater than distance H8, or distance H7 is less than distance H8. Each of the insulating elements 89 has a prescribed exterior height H5 which equals the interior height H6 plus distance H7 plus distance H8. In one embodiment of the interleaved insulator sensor the interior heights H6 of each of the insulating elements 89 have the same value. In another embodiment of the interleaved insulator sensor the interior heights H6 of each of the insulating elements 89 have different values.

In the particular interleaved insulator sensor embodiment exemplified in FIG. 10, the sensor 76 includes two porous ceramic elements 88 and 90 and one insulating element 89. Alternate embodiments of the interleaved insulator sensor (not shown) are also possible where the sensor can include more than two ceramic elements and more than one insulating element (e.g., the sensor can include three ceramic elements and two insulating elements, the sensor can include four ceramic elements and three insulating elements, and so on).

As exemplified in FIG. 10, the interleaved insulator sensor 76 also includes a second number of electrically conductive interface plates 84-87, where this second number is twice the total quantity of porous ceramic elements 88 and 90 that are included within the sensor (e.g., in the interleaved insulator sensor embodiment exemplified in FIG. 10 where the sensor includes two ceramic elements, the sensor will also include four interface plates). More particularly, the sensor 76 includes one half the second number of upper plates 84 and 86 and one half the second number of lower plates 85 and 87. The individual interface plates 84-87 have the same features and attributes as the electrically conductive interface plates described in section 1.2. In other words, each of the interface plates 84-87 includes a third axial opening which is generally centered along the radial axis of the interface plate.

Generally speaking and as exemplified in FIG. 10, the electrically conductive interface plates 84-87 are axially distributed within the interleaved insulator sensor 76 such that the radial axis of each of the interface plates is positioned along the common axis C-C, and each of the ceramic elements 88 and 90 is sandwiched between a different upper plate 84 and 86 and lower plate 85 and 87 such that substantial electrical contact is established between the ceramic element and both the upper and lower plates. More particularly, a different upper plate (e.g., plate 84) is disposed onto the upper electrically conductive coating (e.g., coating 91) on each of the porous ceramic elements (e.g., ceramic element 88) in the stack. A different lower plate (e.g., plate 85) is disposed onto the lower electrically conductive coating (e.g., coating 93) on each of the ceramic elements (e.g., ceramic element 88) in the stack. The insulating elements 89 are interleaved between the ceramic elements 88 and 90 in the stack such that each insulating element holds the lower plate that is disposed onto the lower coating on the ceramic element adjoining the top of the insulating element against this lower coating, and holds the upper plate that is disposed onto the upper coating on the ceramic element adjoining the bottom of the insulating element against this upper coating (e.g., insulating element 89 holds plate 85 against coating 93 on ceramic element 88, and holds plate 86 against coating 92 on ceramic element 90).

As exemplified in FIG. 10 and referring again to FIG. 11, the first axial openings of the porous ceramic elements 88 and 90 combine with the second axial openings of the insulating elements 89 and the third axial openings of the electrically conductive interface plates 84-87 to form a longitudinal cavity within the interleaved insulator sensor 76, where this longitudinal cavity is centered along the common axis C-C and extends from a proximal end 77 of the sensor to a distal end 78 of the sensor. The aforementioned exterior diameter D5 of each of the interface plates 84-87 is set to be less than the aforementioned diameter D3 of the axially-recessed cavity on the top of each of the ceramic elements 88 and 90, and also less than the aforementioned diameter D4 of the axially-recessed cavity on the bottom of each of the ceramic elements, and also less than the diameter D10 of the axially-recessed cavity on the top of each of the insulating elements 89, and also less than the diameter D9 of the axially-recessed cavity on the bottom of each of the insulating elements 89. The top edge 108 of the second upwardly-facing raised rim 104 of each of the insulating elements 89 contacts the bottom edge of the first downwardly-facing raised rim 100 of the ceramic element 88 adjoining the top of the insulating element. The bottom edge 109 of the second downwardly-facing raised rim 105 of each of the insulating elements 89 contacts the top edge of the first upwardly-facing raised rim 99 of the ceramic element 90 adjoining the bottom of the insulating element.

As exemplified in FIG. 10, the aforementioned distance H3 the first upwardly-facing raised rim 98 and 99 extends from the first top horizontal surface of each of the ceramic elements 88 and 90, the aforementioned distance H4 the first downwardly-facing raised rim 100 and 101 extends from the first bottom horizontal surface of each of the ceramic elements, the aforementioned thickness T1 of each of the upper electrically conductive coatings 91 and 92, the aforementioned thickness T2 of each of the lower electrically conductive coatings 93 and 94, the aforementioned thickness T3 of each of the electrically conductive interface plates 84-87, distance H7 and distance H8 are interrelated as follows. Values are selected for distances H3, H4, H7 and H8, and for thicknesses T1, T2 and T3, such that the sum of thicknesses T2 and T3 equals the sum of distances H4 and H7, and the sum of thicknesses T1 and T3 equals the sum of distances H3 and H8. Thus, substantial electrical contact is established between each of the upper plates 84 and 86 and the upper electrically conductive coating 91 and 92 on each of the ceramic elements 88 and 90 in the stack. Substantial electrical contact is also established between each of the lower plates 85 and 87 and the lower electrically conductive coating 93 and 94 on each of the ceramic elements 88 and 90 in the stack.

As exemplified in FIG. 10, the interleaved insulator sensor 76 also generally includes a third number of electrical conductors 80-83, where this third number equals the aforementioned second number (i.e., the number of electrical conductors equals the number of electrically conductive interface plates 84-87). A distal end of each of the electrical conductors 80-83 is electrically attached to a different one of the interface plates 84-87. A proximal end of each of the electrical conductors 80-83 is routed through the longitudinal cavity within the sensor 76 to the proximal end 77 of the sensor. The individual electrical conductors 80-83 have the same features and attributes as the electrical conductors described in section 1.2.

Referring again to FIG. 10, the interleaved insulator sensor 76 can optionally be potted as follows in order to maximize the sensor's operating lifetime, reliability and resistance to shock and vibration. A potting compound 79 can be applied to the sensor 76 such that the compound fills the longitudinal cavity within the sensor, covers the distal end 78 of the sensor, and also covers the proximal end 77 of the sensor. The materials that can be employed for the potting compound are the same as those described in section 1.2.

2.0 Additional Embodiments

While the stacked sensor has been described by specific reference to embodiments thereof, it is understood that variations and modifications thereof can be made without departing from the true spirit and scope of the stacked sensor. By way of example but not limitation, rather than the sensor including a plurality of porous ceramic elements which are hydrophilic, alternate embodiments of the stacked sensor described herein are also possible where the sensor includes a plurality of porous hydrophobic elements, each of which operate as a discrete variable capacitor and exhibit a different known liquid release curve. By way of example, but not limitation, each of the hydrophobic elements can be constructed from a porous polymer plastic material, or each of the hydrophobic elements can be constructed from a ceramic material which has been treated to be hydrophobic. Such alternate embodiments are advantageous since they allow the stacked sensor embodiments to work with both polar and non-polar liquids, and to determine specific dielectric characteristics for these liquids in different physical environments such as different pressures in the porous medium being tested, different temperatures in the medium, and the like.

Additionally, rather than the measurement electronics applying an AC voltage to each of the sensor's porous ceramic elements and then measuring the complex impedance thereof, or the measurement electronics applying a DC voltage to each of the ceramic elements and then measuring the resistance thereof, an alternate embodiment of the stacked sensor described herein is also possible where the measurement electronics operate as a time-domain reflectometer and measure the changes in the impedance and absorption of the ceramic elements caused by various properties of the porous medium being tested (such as its liquid content and salinity, among others).

Figure 9:
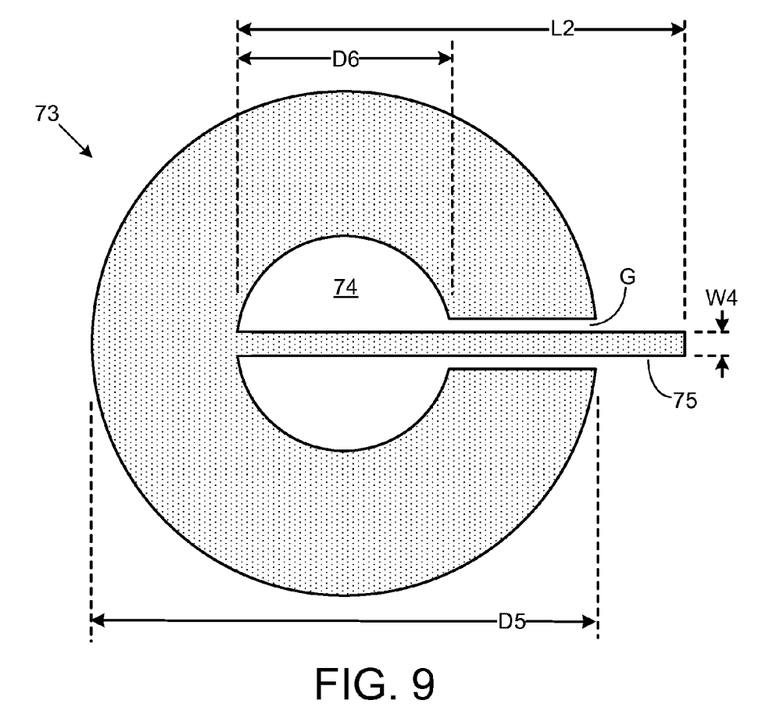
FIG. 9 is a diagram illustrating a standalone top view, in simplified form, of an alternate embodiment of one of the electrically conductive interface plates included within the stacked sensor of FIG. 2.

Additionally and generally speaking, rather than the second number of electrical conductors being wires and the distal end of each wire being electrically attached to a tab on a different one of the electrically conductive interface plates, an alternate embodiment of the stacked sensor described herein is also possible where each of the second number of electrical conductors can be an integrally formed part of the interface plate to which the conductor is electrically attached. More particularly, FIG. 9 illustrates a standalone top view, in simplified form, of an alternate embodiment of one of the interface plates included within the sensor. As exemplified in FIG. 9, this particular embodiment of the interface plate 73 has the aforementioned prescribed exterior diameter D5 and the aforementioned prescribed thickness T3 (not shown), and includes an axial opening 74 which is generally centered along the radial axis of the interface plate. The axial opening 74 has the aforementioned prescribed diameter D6. The interface plate 73 also includes an integrated conductive element 75 which protrudes radially inward toward the center of the axial opening 74 and through a radial gap G which is present in the interface plate. The conductive element 75 has a prescribed length L2 and a prescribed width W4. A variety of sizes can be employed for width W4. In an exemplary embodiment of the stacked sensor width W4 can have the same value as the aforementioned width W3. When the sensor is assembled the conductive element 75 can be folded upward (this folding is not shown) such that it is generally perpendicular to the interface plate 73. In one embodiment of the stacked sensor the size of length L2 can be chosen such that the conductive element 75 is long enough to exit the proximal end of the sensor. In another embodiment of the stacked sensor the size of length L2 can be chosen such that the conductive element 75 is long enough to be attached to the aforementioned connector which can be located at the proximal end of the sensor. It will be appreciated that when the sensor is assembled the various interface plates 73 within the sensor can be successively rotated a prescribed number of degrees about the common axis so that the conductive elements 75 of the interface plates will be radially offset from each other and will not interfere with each other as they travel through the longitudinal cavity toward the proximal end of the sensor.

It is also noted that any or all of the aforementioned stacked sensor embodiments can be used in any combination desired to form additional hybrid embodiments. Although the stacked sensor embodiments have been described in language specific to structural features and/or methodological acts, it is to be understood that the subject matter defined in the appended claims is not necessarily limited to the specific features or acts described heretofore. Rather, the specific features and acts described heretofore are disclosed as example forms of implementing the claims.

Wherefore, what is claimed is:

1. A stacked sensor for testing a porous medium, comprising:
   a plurality of porous ceramic elements, wherein each element operates as a discrete variable capacitor, each element exhibits a different known liquid release curve, and each element comprises a first axial opening, and wherein the elements are stacked one on top of another such that the radial axis of each element is positioned along a common axis;
   a first number of electrically conductive interface plates, wherein each plate comprises a second axial opening, and the first number is one greater than the total quantity of elements, and wherein the plates are axially distributed within the sensor such that,
     the radial axis of each plate is positioned along the common axis,
     the first axial openings of the elements combine with the second axial openings of the plates to form a longitudinal cavity within the sensor which is centered along the common axis and extends from a proximal end of the sensor to a distal end of the sensor, and
     each element is sandwiched between a different pair of plates such that substantial electrical contact is established between the element and both plates in the pair; and
   a second number of electrical conductors, wherein the second number equals the first number, a distal end of each conductor is electrically attached to a different one of the plates, and a proximal end of each conductor is routed through the cavity to the proximal end of the sensor.

2. The stacked sensor of claim 1, wherein the number of elements is five, said five elements comprising:
   a topmost element;
   a first intervening element which is immediately beneath the topmost element;
   a second intervening element which is immediately beneath the first intervening element;
   a third intervening element which is immediately beneath the second intervening element; and
   a bottommost element which is immediately beneath the third intervening element.

3. The stacked sensor of claim 2, wherein,
   the topmost element comprises a ½ bar high flow pore structure,
   the first intervening element comprises a 1 bar high flow pore structure,
   the second intervening element comprises a 2 bar high flow pore structure,
   the third intervening element comprises a 5 bar high flow pore structure, and
   the bottommost element comprises a 15 bar high flow pore structure.

4. The stacked sensor of claim 1, wherein either the number of elements is less than five, or the number of elements is greater than five.

5. The stacked sensor of claim 1, wherein each element further comprises a continuous, interconnected system of pores, the pores have a known distribution throughout the element, and the pores have a known size distribution which is different than that of the other elements.

6. The stacked sensor of claim 1, further comprising a potting compound which is applied to the sensor such that the compound fills the cavity, covers the distal end of the sensor, and covers the proximal end of the sensor.

7. The stacked sensor of claim 1, further comprising:
   a temperature sensing device; and
   an additional pair of electrical conductors, wherein a distal end of said conductors is electrically attached to said device, and a proximal end of said conductors is routed through the cavity to the proximal end of the sensor.

8. The stacked sensor of claim 7, wherein either,
   the proximal end of each of the second number of electrical conductors and the proximal end of the additional pair of electrical conductors exit the cavity at the proximal end of the sensor, or
   the proximal end of each of the second number of electrical conductors and the proximal end of the additional pair of electrical conductors are electrically attached to a connector which is located at the proximal end of the sensor.

9. The stacked sensor of claim 1, wherein each plate is constructed from a material comprising one of: copper; or brass; or stainless steel; or a nickel alloy; or aluminum; or gold; or platinum; or silver.

10. The stacked sensor of claim 1, wherein each element further comprises a radially exterior shape comprising one of: a circular shape; or an oval shape; or a triangular shape; or a square shape; or a rectangular shape; or a pentagonal shape; or a hexagonal shape; or an octagonal shape.

11. The stacked sensor of claim 1, wherein the first axial opening of each element comprises a radial shape comprising one of: a circular shape; or an oval shape; or a triangular shape; or a square shape; or a rectangular shape; or a pentagonal shape; or a hexagonal shape; or an octagonal shape.

12. The stacked sensor of claim 1, wherein,
   each element further comprises a radially exterior shape comprising a first shape,
   the first axial opening of each element comprises a radial shape comprising a second shape, and either,
   the first shape is the same as the second shape, or the first shape is different than the second shape.

13. The stacked sensor of claim 1, wherein,
each element further comprises a first radially exterior shape,
each plate further comprises a second radially exterior shape, and either,
the first radially exterior shape is the same as the second radially exterior shape, or
the first radially exterior shape is different than the second radially exterior shape.

14. The stacked sensor of claim 1, wherein,
the first axial opening of each element comprises a first radial shape,
the second axial opening of each plate comprises a second radial shape, and either,
the first radial shape is the same as the second radial shape, or
the first radial shape is different than the second radial shape.

15. The stacked sensor of claim 1, further comprising one or more of:
a third number of signal buffers and a power source for powering the buffers, wherein the third number equals the first number and each buffer is electrically connected in series with a different one of the conductors; or
analog-to-digital converter and digital signal processing electronics, and a power source for powering said electronics.

16. The stacked sensor of claim 1, wherein,
the stacking of elements one on top of another forms one or more adjoining pairs of elements,
each adjoining pair of elements comprises an upper element and a lower element,
the first axial opening of each element is centered along the radial axis of the element,
the second axial opening of each plate is centered along the radial axis of the plate, and
each element further comprises:
a radially outer vertical edge which is exposed to the porous medium;
a top horizontal surface;
a bottom horizontal surface;
an upwardly-facing raised rim which is positioned on the top horizontal surface along the radially outer vertical edge, said rim forming an axially-recessed cavity on the top of the element;
a downwardly-facing raised rim which is positioned on the bottom horizontal surface along the radially outer vertical edge, said rim forming an axially-recessed cavity on the bottom of the element;
an upper electrically conductive coating which is evenly applied onto the top horizontal surface; and
a lower electrically conductive coating which is evenly applied onto the bottom horizontal surface, wherein
a bottom edge of the downwardly-facing raised rim of the upper element in each adjoining pair of elements contacts a top edge of the upwardly-facing raised rim of the lower element in said pair.

17. The stacked sensor of claim 16, wherein,
each element further comprises an exterior diameter D2,
the upwardly-facing raised rim of each element comprises a radial width W1 and extends upward a distance H3 from the top horizontal surface of the element,
the axially-recessed cavity on the top of each element comprises a diameter D3 which equals the diameter D2 minus twice the width W1,
the downwardly-facing raised rim of each element comprises a radial width W2 and extends downward a distance H4 from the bottom horizontal surface of the element,
the axially-recessed cavity on the bottom of each element comprises a diameter D4 which equals the diameter D2 minus twice the width W2,
the upper electrically conductive coating comprises a thickness T1,
the lower electrically conductive coating comprises a thickness T2,
each plate further comprises an exterior diameter D5 and a thickness T3,
the sum of thicknesses T1, T2 and T3 equals the sum of distances H3 and H4,
diameter D5 is less than both diameter D3 and diameter D4, and
the first number of electrically conductive interface plates comprises a topmost plate, one or more intervening plates, and a bottommost plate, wherein,
the topmost plate is disposed onto the upper electrically conductive coating on the upper element in a topmost adjoining pair,
each intervening plate is disposed between a different adjoining pair of elements such that said plate is sandwiched between the lower electrically conductive coating on the upper element in said adjoining pair and the upper electrically conductive coating on the lower element in said adjoining pair, and
the bottommost plate is disposed onto the lower electrically conductive coating on the lower element of a bottommost adjoining pair.

18. The stacked sensor of claim 17, wherein either,
widths W1 and W2 have the same value, or
width W1 is greater than width W2, or
width W1 is less than width W2.

19. The stacked sensor of claim 17, wherein either,
distances H3 and H4 have the same value, or
distance H3 is greater than distance H4, or
distance H3 is less than distance H4.

20. The stacked sensor of claim 16, wherein,
each element further comprises an interior height which is the distance between the top and bottom horizontal surfaces, and either,
the interior heights of each of the elements have the same value, or
the interior heights of each of the elements have different values.

21. The stacked sensor of claim 16, wherein the upper and lower electrically conductive coatings comprise an electrically conductive epoxy.

22. The stacked sensor of claim 1, wherein either,
each plate further comprises a tab which protrudes radially inward toward the center of the second axial opening, the conductors comprise wires, and the distal end of each wire is electrically attached to the tab on the different one of the plates, or
each conductor is an integrally formed part of the plate to which the conductor is electrically attached.

23. The stacked sensor of claim 1, wherein,
the first axial opening of each element comprises a diameter D1, and
the second axial opening of each plate comprises a diameter D6 which is less than or equal to diameter D1.

24. A stacked sensor for testing a porous medium, comprising:

a plurality of porous hydrophobic elements, wherein each element operates as a discrete variable capacitor, each element exhibits a different known liquid release curve, and each element comprises a first axial opening, and wherein the elements are stacked one on top of another such that the radial axis of each element is positioned along a common axis;

a first number of electrically conductive interface plates, wherein each plate comprises a second axial opening, and the first number is one greater than the total quantity of elements, and wherein the plates are axially distributed within the sensor such that,    the radial axis of each plate is positioned along the common axis,    the first axial openings of the elements combine with the second axial openings of the plates to form a longitudinal cavity within the sensor which is centered along the common axis and extends from a proximal end of the sensor to a distal end of the sensor, and    each element is sandwiched between a different pair of plates such that substantial electrical contact is established between the element and both plates in the pair; and a second number of electrical conductors, wherein the second number equals the first number, a distal end of each conductor is electrically attached to a different one of the plates, and a proximal end of each conductor is routed through the cavity to the proximal end of the sensor.

25. The stacked sensor of claim 24, wherein each element is constructed from a material comprising one of: a polymer plastic material; or a ceramic material which has been treated to be hydrophobic.

26. A stacked sensor for testing a porous medium, comprising:

a plurality of porous ceramic elements, wherein each ceramic element operates as a discrete variable capacitor, each ceramic element exhibits a different known liquid release curve, and each ceramic element comprises a first axial opening;

a first number of non-porous and electrically non-conductive insulating elements, wherein each insulating element comprises a second axial opening, the first number is one less than the total quantity of ceramic elements, the radial axis of each of the insulating elements and each of the ceramic elements is positioned along a common axis, and the insulating elements are interleaved between the ceramic elements such that each insulating element is sandwiched between a different pair of ceramic elements;

a second number of electrically conductive interface plates comprising one half the second number of upper plates and one half the second number of lower plates, wherein each interface plate comprises a third axial opening, and the second number is twice said total quantity, and wherein the interface plates are axially distributed within the sensor such that,    the radial axis of each interface plate is positioned along the common axis,    the first axial openings of the ceramic elements combine with the second axial openings of the insulating elements and the third axial openings of the interface plates to form a longitudinal cavity within the sensor which is centered along the common axis and extends from a proximal end of the sensor to a distal end of the sensor, and    each ceramic element is sandwiched between a different upper plate and lower plate such that substantial electrical contact is established between the ceramic element and both the upper and lower plates; and a third number of electrical conductors, wherein the third number equals the second number, a distal end of each conductor is electrically attached to a different one of the interface plates, and a proximal end of each conductor is routed through the cavity to the proximal end of the sensor.

\* \* \* \* \*